United States Patent [19]

Suhov

[11] Patent Number: 4,852,376

[45] Date of Patent: Aug. 1, 1989

[54] LOCKBOLT INSTALLATION TOOL WITH CARTRIDGE FEED

[75] Inventor: Boris P. Suhov, Mission Viejo, Calif.

[73] Assignee: Huck Manufacturing Company, Irvine, Calif.

[21] Appl. No.: 104,705

[22] Filed: Oct. 5, 1987

[51] Int. Cl.⁴ .............................................. B21D 9/05
[52] U.S. Cl. .................................. 72/391; 72/453.17; 29/243.53
[58] Field of Search ............... 72/391, 453.17, 453.19; 29/243.53, 809; 227/112

[56] References Cited

U.S. PATENT DOCUMENTS

| | | | |
|---|---|---|---|
| 2,592,636 | 4/1952 | Aherne-Heron | 72/391 |
| 3,298,585 | 1/1967 | Mohrke et al. | 227/112 |
| 3,553,816 | 1/1971 | Arnshav | 227/112 |
| 3,733,882 | 5/1973 | Klein | 72/391 |
| 4,005,519 | 2/1977 | Di Maio et al. | 72/391 |
| 4,044,462 | 8/1977 | Anselmo | 29/809 |
| 4,604,889 | 8/1986 | Sukharevsky | 72/391 |
| 4,643,344 | 2/1987 | Kaita et al. | 227/112 |
| 4,747,294 | 5/1988 | Schwartz et al. | 29/809 |
| 4,754,643 | 7/1988 | Weeks, Jr. et al. | 29/809 |

FOREIGN PATENT DOCUMENTS

| 2148396 | 4/1973 | Fed. Rep. of Germany | 227/112 |
|---|---|---|---|
| 0227335 | 12/1984 | Japan | 29/809 |

Primary Examiner—David Jones
Attorney, Agent, or Firm—Lawrence J. Shurupoff

[57] ABSTRACT

A manually-operated fastener installation tool is provided with a self-contained cartridge or magazine for feeding lockbolt collars to an installation position adjacent the tool nosepiece. A fixed, inflexible feed path directs the collars from the cartridge towards the nosepiece to eliminate the jamming which occurs with conventional flexible feed tubes. The entire collar feed path is pivotally mounted within the tool to avoid complex shuttling movements of the collars across transition regions and discontinuities in the feed path to further reduce jamming.

10 Claims, 10 Drawing Sheets

LOCKBOLT INSTALLATION TOOL WITH CARTRIDGE FEED

BACKGROUND OF THE INVENTION

1. Field of the Invention

This invention relates generally to a lockbolt installation tool and more particularly concerns a portable tool which automatically feeds a lockbolt collar from a self-contained cartridge or magazine through a pivotable delivery tube to an installation position adjacent the tool nosepiece.

2. Description of Prior Developments

Abutting workpieces are commonly joined together with the use of pin and collar type fasteners known as lockbolts. The lockbolt pin is inserted through an opening in each workpiece so that the head of the pin contacts an exposed surface of one workpiece and the tail of the pin projects through the other workpiece. The collar is then fitted over the pintail and the fastener is set by axially pulling the pin with an installation tool and applying the reaction force to the collar.

The reaction force locks the collar to the pin by plastically deforming or swaging the collar into locking grooves formed in the pin. Details of this operation are set forth in U.S. Pat. No. 2,531,048, the specification of which is incorporated herein by reference. This assembly operation is labor intensive as the pin and collar are typically located by hand prior to setting.

To partially automate this process various arrangements have been designed to automatically feed the collar to an appropriate position within the installation tool so that the collar and tool may be simultaneously positioned around the pin to facilitate the swaging process. Although these automatic collar feeders present an improvement over a completely manual operation, several drawbacks have been associated with their use. The major drawback is the frequency with which these collar feeding mechanisms become jammed.

Conventional collar feeding mechanisms have used a flexible external hose for interconnecting a vibratory collar sorting bin or collar reservoir with a feed port on the body of the fastening tool. Collars have been found to jam at the interface between the tool body and the external hose due to the discontinuity in the collar feed path at this junction. Moreover, once a collar has passed through the feed port and entered the tool, various steps, transitions or other discontinuities in the feed path present additional obstacles to the travel of the collar and have also been a cause of jamming.

The use of an external feed hose presents additional installation problems. The flexible hose can become kinked resulting in a misfeed. Furthermore, a tool operator or co-worker can accidently step on the flexible hose thereby cutting off the supply of collars to the tool. In some cases the manipulation of the tool through awkward positions can cause the collar delivery hose to bind or kink. Because of the limited space within which some lockbolts are located, the feed tube can complicate or prevent tool access to the fastener by interfering with the workpiece or other structures adjacent the fastener installation site.

Accordingly, a need exists for an automated jam-resistant collar feed mechanism for a lockbolt installation tool which facilitates the placement of a collar over a pin, yet which allows easy access to all installation sites.

SUMMARY OF THE INVENTION

The present invention has been developed to meet the needs noted above and therefore has as an object the provision of a cartridge-fed collar feeding mechanism which avoids the use of external feed hoses.

Another object is to provide a collar feed path which is substantially fixed in configuration and rigid throughout so as to avoid shuttling of the collar across discontinuities in the feed path.

Still another object is to provide a self-contained sealed collar cartridge having a jam-resistant feed path.

Another object is to provide a collar feed mechanism which maintains a feed path which is fixed relative to the collars yet which undergoes linear and pivotal motion during tool actuation.

Yet another object is to eliminate the need for external collar sources such as vibrator sorting bins.

BRIEF DESCRIPTION OF THE DRAWINGS

Various other objects, features and attendant advantages of the present invention will be more fully appreciated as the same becomes better understood from the following detailed description when considered in connection with the accompanying drawings, in which like reference characters designate like or corresponding parts through the several views and wherein.

DETAILED DESCRIPTION OF THE PREFERRED EMBODIMENT

The invention will now be described in conjunction with the drawings, beginning with FIGS. 1, 1a and 2 which show an installation tool (1) for setting a pin and collar type fastener (2) of the lockbolt variety. The tool is provided with a nose assembly (3) of conventional design such as shown in U.S. Pat. No. 3,362,211, the disclosure of which is incorporated herein by reference. The nose assembly includes an anvil (5), collet (7) and jaws (9). The collet is connected to a conventional hydraulically actuated piston assembly (11) of the type shown in U.S. Pat. 3,362,211.

A piston (13) is mounted within the tool body (15) for driving the nose assembly and setting the fastener. During tool actuation, hydraulic feed line (17) feeds oil or the like to the front face of the piston while hydraulic return line (19) receives fluid expelled from chamber (21).

Figure 2:
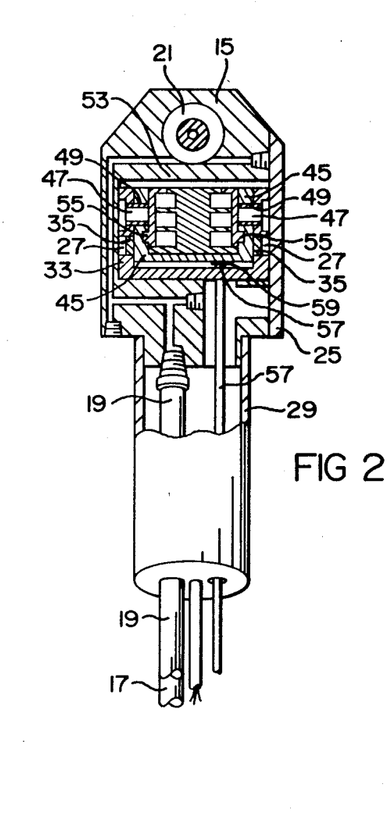
FIG. 2 is a transverse sectional view taken through line A—A of FIG. 1.
Figure 2A:
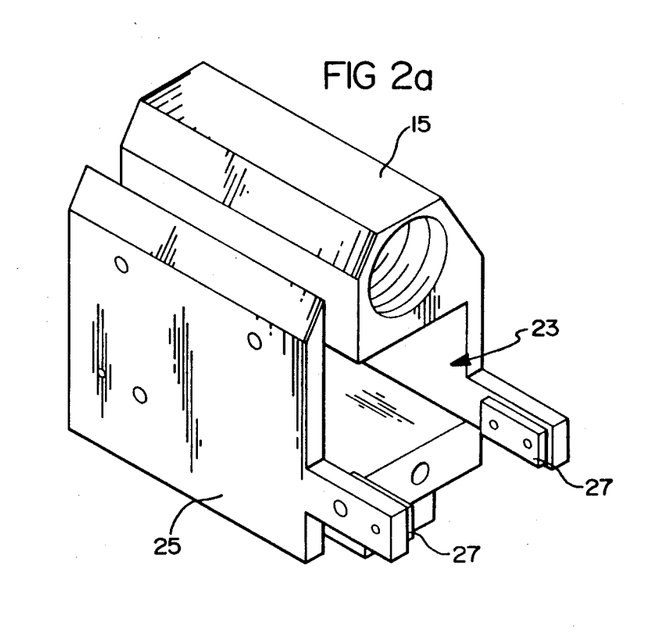
FIG. 2a is a perspective view of the tool body.

As best seen in FIGS. 2 and 2a, the tool body defines a three-sided channel (23) which is closed by cover plate (25). Both the tool body and the cover plate are provided with inwardly projecting guide rails (27) disposed on their respective inner walls. The tool body is secured to a handle (29) fitted with a trigger switch (31) for actuating a pressurized source of fluid for powering the piston in a known fashion.

Figure 1:
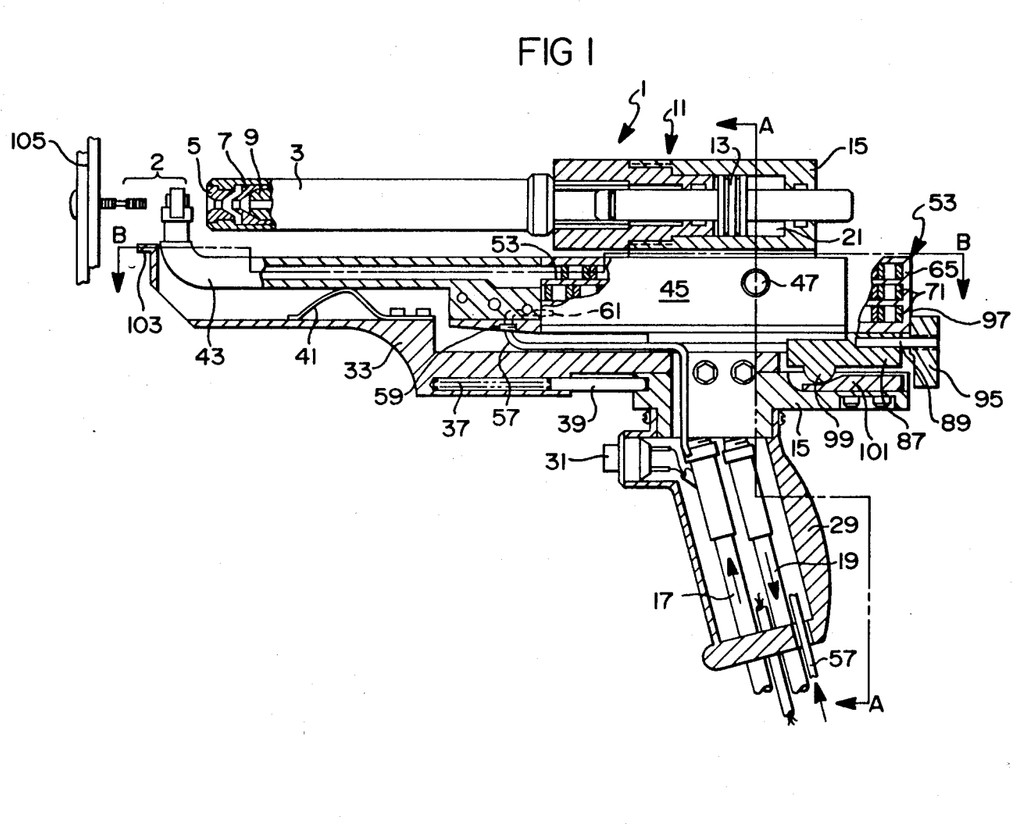
FIG. 1 is a longitudinal sectional plan view through the installation tool.
Figure 1A:
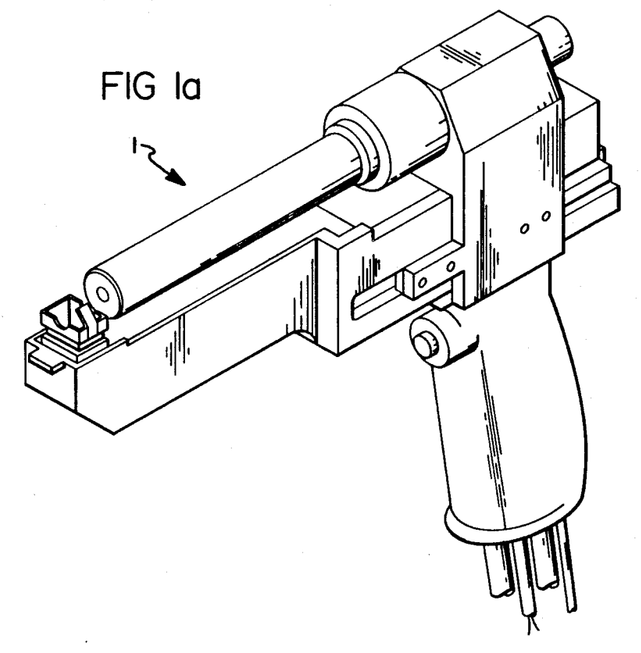
FIG. 1a is a perspective view, partly in section, of the installation tool.
Figure 3:
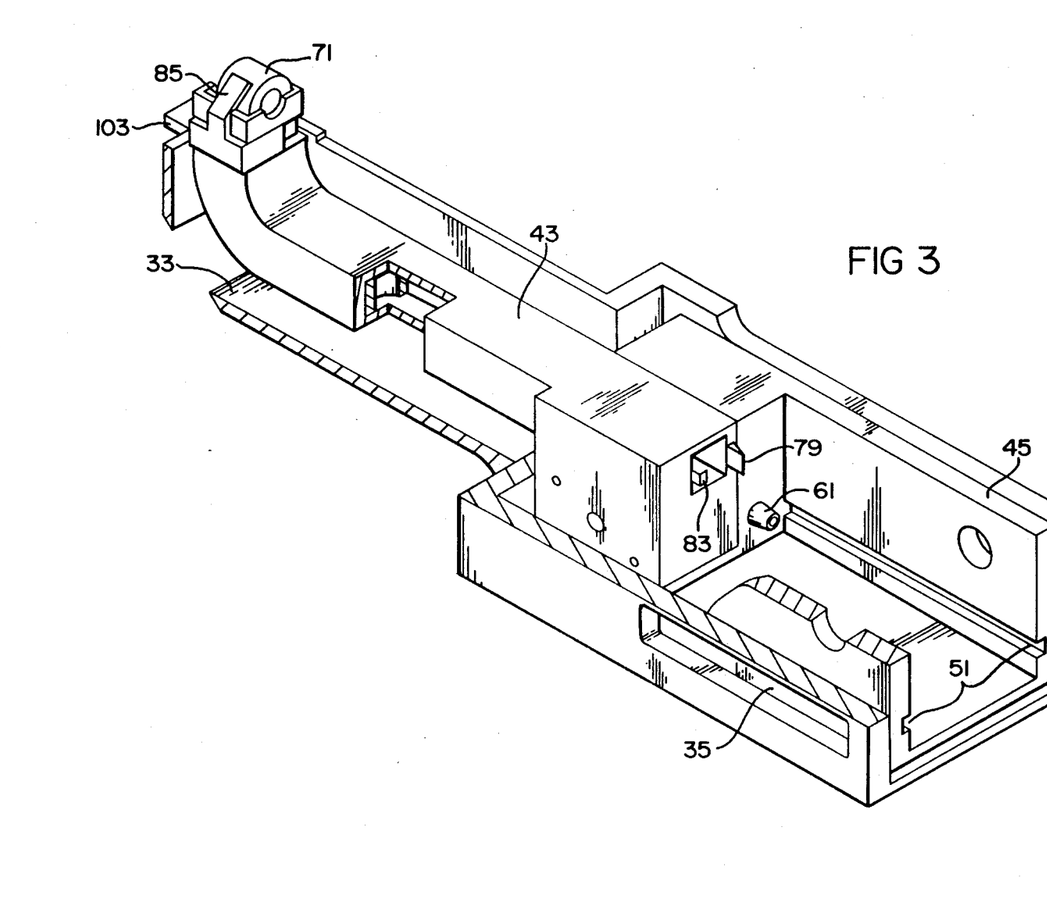
FIG. 3 is a perspective view, partly in section, of the cartridge holder and delivery tube mounted within the trough.

An elongated trough (33) is slidably mounted within the tool body as seen in FIGS. 1, 2 and 3. The side walls of the trough are formed with a pair of elongated parallel guide slots (35) as shown in FIGS. 2 and 3. The guide rails (27) are closely fitted within the guide slots to secure the trough to the tool body and to limit the movement of the trough relative to the tool body to a linear translation.

A biasing element such as coil spring (37) (FIG. 1) is fitted within a bore in the trough to bias plunger (39) against the tool body to form a trough return mechanism. Another biasing element such as leaf spring (41) is disposed between the trough and feed tube (43) to serve as a feed tube return mechanism. The feed tube is secured to a cartridge holder (45) which is pivotally mounted within the trough with pivot pins (47) and bearings (49).

Figure 8:
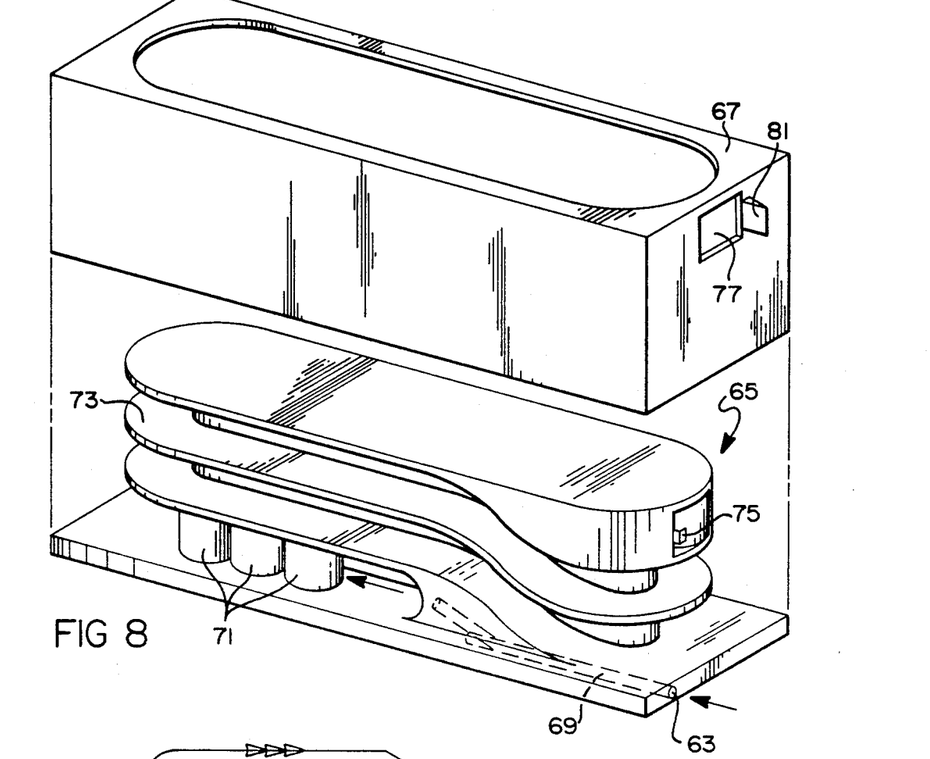
FIG. 8 is a perspective view of the collar cartridge showing the cartridge insert and cartridge cover.

As seen in FIGS. 2 and 3, the inner walls of the cartridge holder are provided with cartridge guides such as parallel channels (51) for aligning cartridge (53) therebetween. The cartridge is provided with complimentary ribs (55) which fit within the channels and accurately align the cartridge within the cartridge holder. A flexible air hose (57) (FIG. 1) is connected to a fitting (59) in the floor of the cartridge holder. As seen in FIGS. 1, 3 and 8, a hollow nipple (61) projects from the floor of the cartridge holder to mate with an air intake port (63) located in the lower front wall of the cartridge body (65).

Figure 9:
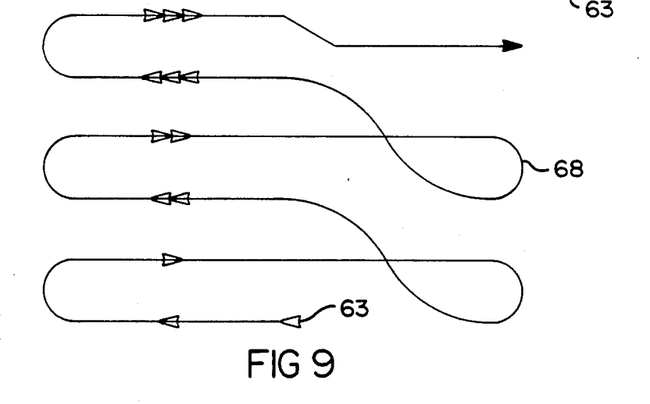
FIG. 9 is a schematic diagram of the collar feed path defined by the cartridge insert.
Figures 10, 11:
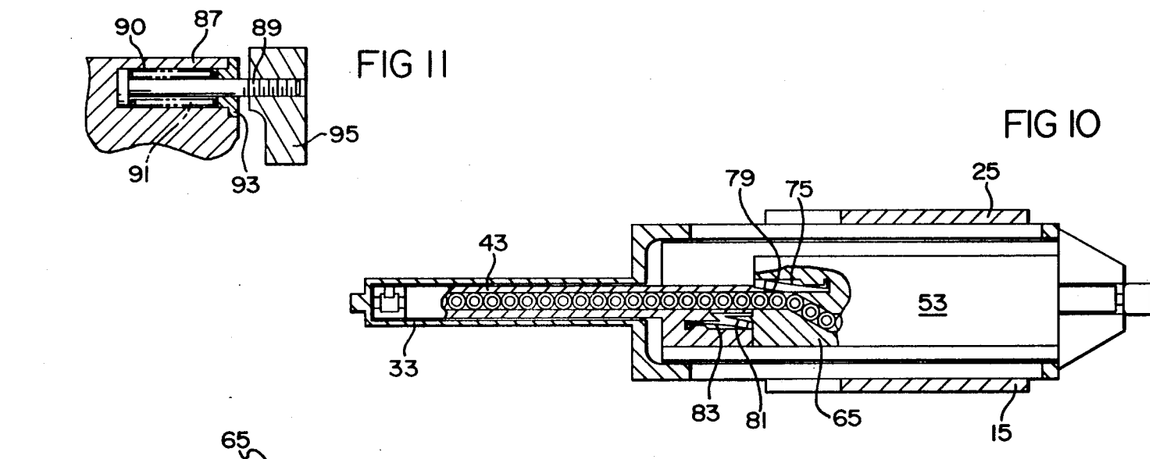
FIG. 10 is a sectional plan view taken through line B—B of FIG. 1 showing the interconnection between the cartridge and the delivery tube.
FIG. 11 is an enlarged fragmental sectional view of the cartridge locking assembly.
Figure 12:
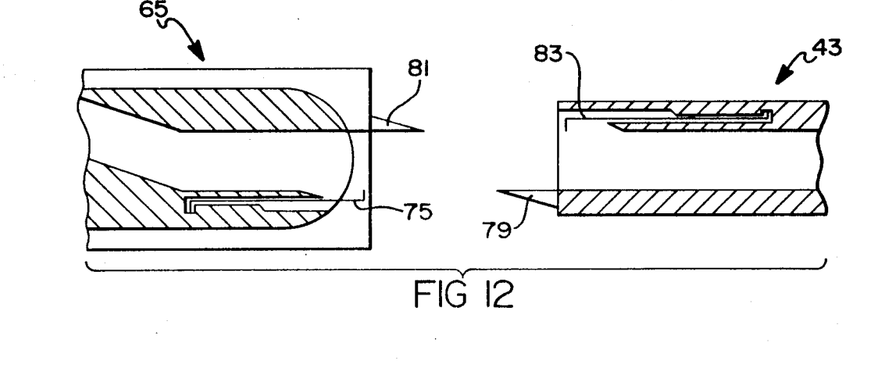
FIG. 12 is a schematic fragmental sectional view through the cartridge body and feed tube showing their relative interengagement.

A cartridge cover (67) (FIG. 8) snugly encloses the cartridge body to define the roughly spiral flow path (68) shown in FIG. 9. The cartridge body and cartridge cover provide a self-contained cartridge assembly which conveniently stores collars and eliminates the need for external collar feeders and flexible feed lines. Air entering intake port (63) is directed through bore (69) to force a string of abutting collars (71) to follow the contours of the spiral tiered ramp structure (73) formed within the cartridge insert. Initially, the cartridge will be completely loaded with collars throughout the entire extent of the tiered ramp. A retaining leaf spring (75) prevents the collars from escaping the cartridge through window (77) prior to insertion of the cartridge within the cartridge holder.

When the cartridge is inserted within the cartridge holder, nipple (61) snugly nests within air intake port (63) to complete a sealed flow path therebetween. At the same time a wedge-shaped finger (79) (FIGS. 3, 8, 10 and 12) projecting from the feed tube (43) engages, cams aside and deflects spring (75) to allow the collars to exit the cartridge through window (77). As finger (79) contacts spring (75), a second finger (81) projecting from the cartridge contacts, cams aside and deflects leaf spring (83) (FIG. 3) disposed within the feed tube. This allows a string of individual collars to exit through window (77) and travel through the feed tube under the pressure of the air flowing through bore (69) and along the flow path (68). Restraining spring (83) prevents any unused collars from falling out of the feed tube upon disengagement of the cartridge from the cartridge holder and feed tube assembly.

As the collars travel from the cartridge through the feed tube the leading collar will eventually contact a resilient collar positioning member such as leaf spring (85) (FIG. 3) connected to the end of the feed tube. The positioning member coaxially aligns the leading collar with the nose assembly so that placement of the collar over a pin will result in the fastener pintail entering the open channel of the nose assembly. As soon as the pintail enters the nose assembly the feed tube is pivoted downwardly, as discussed further below, and the positioning member (85) deflects upwardly to allow the collar to break away from the feed tube.

When the leading collar is released from the feed tube the entire string of collars, up to 100 or more, simultaneously advance along the feed tube and spiral flow path for a distance equal to the diameter of the collars. This collar advancement continues with each actuation of the tool until the supply of collars is exhausted. At this time the cartridge is removed from the cartridge holder and a new fully loaded cartridge is inserted within the cartridge holder for setting additional fasteners.

In order to secure the cartridge within the cartridge holder a locking mechanism is provided on the rear of the cartridge holder. A plate (87) (FIGS. 1 and 11) is fastened to the bottom of the cartridge holder and projects rearwardly to receive a plunger (89) within bore (90). A coil spring (91) biasses the head of the plunger forwardly against the resistance of bore plug (93). The tail of the plunger is pinned to a handle lock (95) which may be pulled rearwardly against the bias of spring (91) and rotated to engage and disengage the rear wall (97) of the cartridge. The handle is shown in its closed or locked position biasing the cartridge against the cartridge holder in FIG. 1 and in its open or loading position in FIG. 4. The depth of bore (90) and length of plunger (89) may be set at any desired value to accommodate cartridges of varying lengths and collar capacities.

A cam follower (99) is provided on the bottom rear portion of the cartridge holder such as on plate (87). Preferably, the cam follower is arcuate in profile such as the semi-cylindrical cam follower depicted in FIG. 1. The axis of the semi-cylinder is disposed transversely across the bottom of the cartridge holder.

A cam (101) is provided on the lower rear portion of the tool body (15) to engage the cam follower. The cam is formed with a rewardly inclined ramp surface having a generally wedge-shaped longitudinal cross section to provide for smooth actuation between the cam and cam follower.

Figure 4:
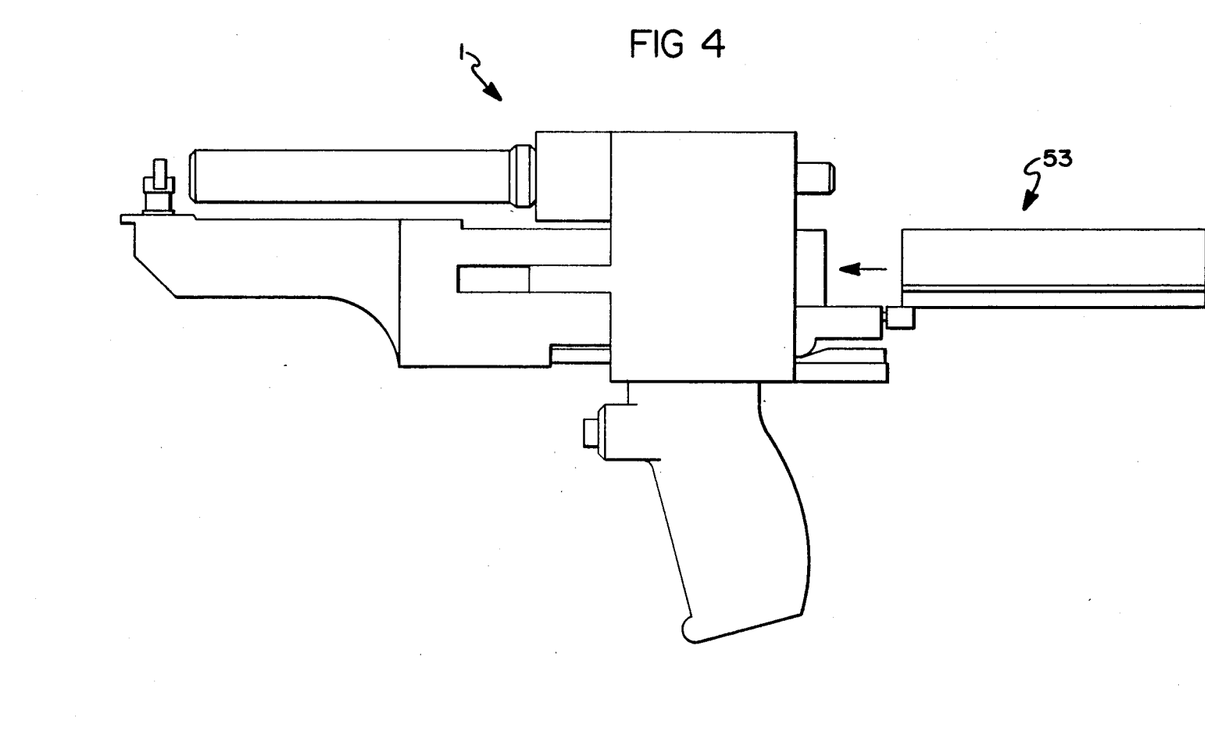
FIG. 4 is a schematic view of the installation tool showing the cartridge in a loading position.
Figure 5:
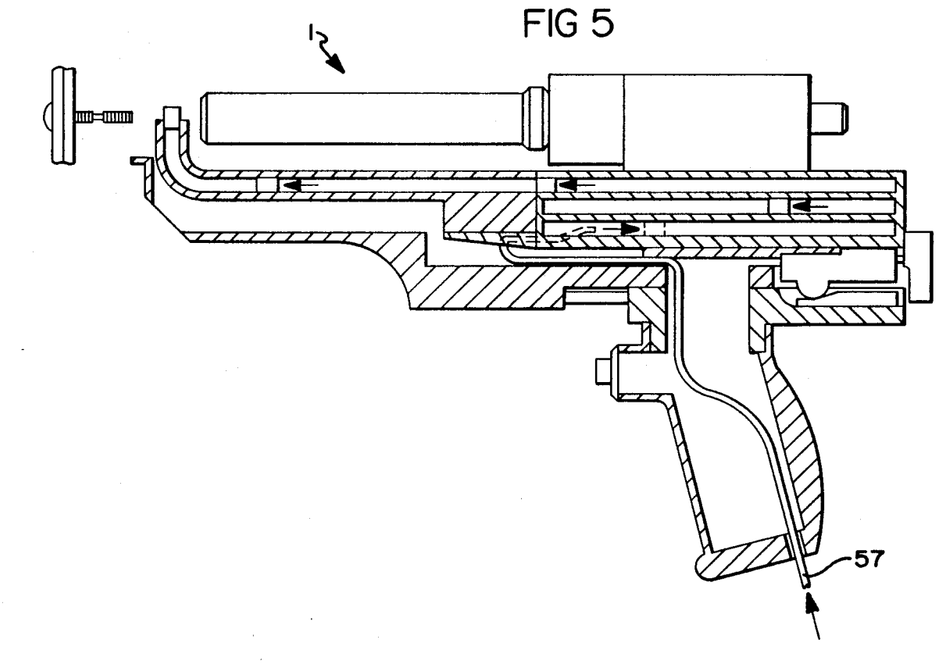
FIG. 5 is a schematic view, partly in section, of the installation tool feeding collars to the delivery tube.
Figure 6:
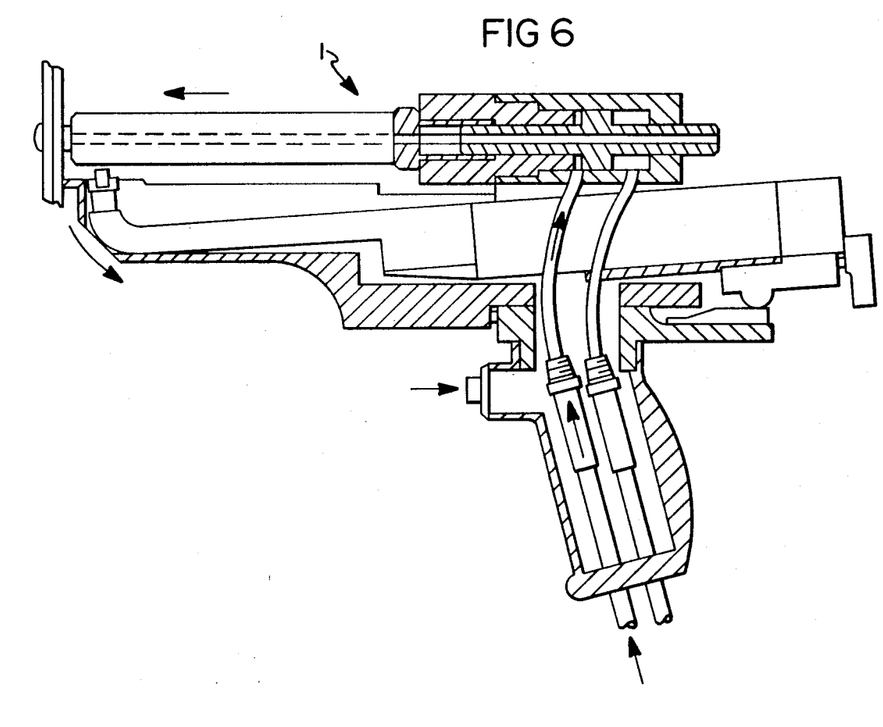
FIG. 6 is a schematic view of the installation tool in an operative position ready for actuation of the setting or pulling stroke.

In use, the handle lock (95) is rotated to its open or loading position to allow for insertion of the cartridge as shown in FIG. 4. Once the cartridge is loaded and the handle is pulled back to clear the cartridge, the handle may be rotated and released to return to its locked position against the cartridge. As this locking occurs, the collars are blown through the delivery tube with a constant supply of low pressure air from air hose (57) so that the first or lead collar is aligned and retained adjacent the nose assembly by positioning member (85) as shown in FIG. 5. An operator then positions the installation tool against the workpiece so that the collar encircles the pin and the pin enters the nose assembly as seen in FIG. 6.

As soon as trough lip (103) (FIG. 1) abuts the workpiece (105), a reaction force is applied to the handle (29) and tool body (15) via plunger (39). As the operator continues to push forwardly on the handle, the plunger (39) recedes within the bore in the trough. At the same time, the handle advances forwardly toward the workpiece and the cam (101) begins to lift the cam follower (99) upwardly along the inclined cam surface. This lifting movement causes the cam (101), cartridge holder (45), cartridge (53), feed tube (43) and handle lock (95) to rotate about the pivot pins (47) as represented in FIG. 6. The pivoting movement causes the tip of the feed tube to dip downwardly and away from the collar and nose assembly thereby allowing the nose assembly to advance forwardly without contacting the feed tube and allowing the pintail to engage the jaws disposed within the nose assembly.

As the handle initially advances toward the workpiece the trough (33) is prevented from pivoting by the guide rails (27) which linearly slide within the slots (35) formed in the trough. In this manner, the trough remains generally in a fixed position against the workpiece during the pivoting and reciprocatory movements of the other tool components during tool actuation. Since the cartridge holder is pivotally fixed to the trough, the cartridge holder, cartridge and feed tube pivot within the trough as the operator advances the handle (29) and tool body (15) toward the workpiece. When the feed tube dips downwardly, the collar is released from the positioning member spring (85) and the nose assembly is in proper position for setting the collar about the pin.

Figure 7:
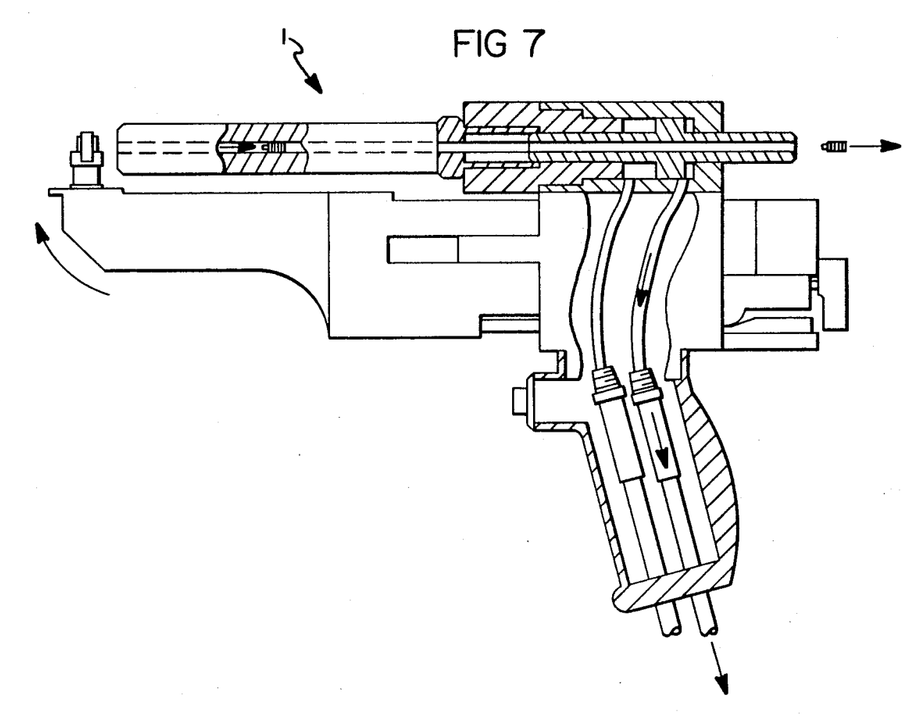
FIG. 7 is a schematic view of the installation tool ejecting a pintail after a collar has been swaged around the pin.

At this point the operator depresses the trigger switch (31) to release hydraulic fluid from a pressurized reservoir and drive the piston and nose assembly rearwardly thereby swaging the collar over the pin in a known manner. As seen in FIG. 7, at the conclusion of the piston's stroke, the end of the pintail is broken off and ejected through a central bore leading from the nose assembly jaws through the rear of the piston.

After the fastener is set, the operator removes the tool from the workpiece by moving handle (29) rearwardly thereby allowing the feed tube to return to its initial position under the biasing force of spring (41). The trough also returns to its initial position under the biasing force of spring (37). At this point the tool is ready to be positioned over another pintail as a new collar has already advanced against the retaining spring (85) upon release of the prior collar.

Since the delivery tube is fixed to and moves with the cartridge, cartridge holder and feed tube, these elements pivot together as one body. In this manner a fixed feed path is maintained from the supply source of the collars, i.e. the cartridge, to the exit point of the collars from the tool. This arrangement significantly reduces jamming by eliminating any shuttling movements of the collar by complex mechanisms. Jamming is also reduced by the relatively rigid, inflexible walls of the feed path which are not susceptible to bending or kinking. Moreover, in contrast to tubular feed lines which coaxially direct collars along a path of circular cross section, the cartridge (53) and feed tube (43) direct collars in a direction perpendicular or transverse to their axes along a feed path having a rectangular cross section. In transporting collars in this transverse manner, the feed path is simplified as the collar need not be shuttled or reoriented when it reaches the positioning member (85).

Obviously, numerous modifications and variations of the present invention are possible in light of the above teachings. It is therefore to be understood that within the scope of the appended claims, the invention may be practiced otherwise than as specifically described herein.

What is claimed is:

1. An installation tool for setting a pin and collar type fastener on a workpiece, said tool comprising:
   a body member;
   fastener storage means for storing a plurality of fastener members within said tool;
   fastener installation means provided on said body member; and
   fastener delivery means mounted on said body member for transferring said fastener members from said storage means to said installation means, said delivery means comprising workpiece engagement means for engaging said workpiece and pivoting said delivery means about said body member so as to avoid contact between said delivery means and said installation means during setting of said fastener.

2. The tool of claim 1, wherein said fastener installation means comprises a piston-actuated nose assembly.

3. The tool of claim 1, wherein said storage means comprises a self-contained cartridge.

4. The tool of claim 3, wherein said cartridge comprises air intake means for driving said fastener members through said cartridge with a flow of air.

5. The tool of claim 1, further comprising pivot means for pivoting said storage means within said body member.

6. The tool of claim 1, wherein said delivery means comprises a feed tube fixed to said storage means.

7. The tool of claim 6, wherein said feed tube and said storage means define a rigid feed path.

8. The tool of claim 1, further comprising cam means operatively associated with said body member and said storage means for pivoting said storage means with respect to said body member.

9. The tool of claim 1, further comprising fastener retaining means provided on said storage means for preventing said fastener members from exiting said storage means, and means for engaging said fastener retaining means operatively associated with said body member, such that placement of said storage means within said tool allows said fastener members to exit said storage means.

10. An installation tool for setting apin and collar type fastener on a workpiece, said tool comprising:
    a body member;
    fastener storage means for storing a plurality of fastener members within said tool;
    fastener installation means provided on said body member;
    fastener delivery means mounted on said body member for transferring said fastener members from said storage means to said installation means; and
    workpiece engagement means provided on said tool of engaging said workpiece and effecting pivoting movement of said delivery means with respect to said body member so as to avoid contact between said delivery means and said installation means during setting of said fastener.

* * * * *

UNITED STATES PATENT AND TRADEMARK OFFICE
CERTIFICATE OF CORRECTION

PATENT NO. : 4,852,376
DATED : August 1, 1989
INVENTOR(S) : Boris P. Suhoy

It is certified that error appears in the above-identified patent and that said Letters Patent is hereby corrected as shown below:

Column 6, line 63, claim 10 "of" should read "for".

Signed and Sealed this

Sixteenth Day of April, 1991

Attest:

HARRY F. MANBECK, JR.

Attesting Officer

Commissioner of Patents and Trademarks